US012564438B2

(12) United States Patent
Cheng et al.

(10) Patent No.: US 12,564,438 B2
(45) Date of Patent: Mar. 3, 2026

(54) ENERGIZED CORERS WITH POWERED CONVEYING

(71) Applicant: Medtronic Advanced Energy LLC, Minneapolis, MN (US)

(72) Inventors: Xiaoming Cheng, Keller, TX (US); Darren L. Davis, Memphis, TN (US); Amy Bradley, Westford, MA (US); Yeung Chow, Longmont, CO (US); Anjali Dhiman, Commerce City, CO (US); Roger D. Greeley, Portsmouth, NH (US); Bradley W. Jacobsen, Erie, CO (US); Yahia Laouar, Superior, CO (US); Prakash Manley, Arvada, CO (US); Martin Masson, Keller, TX (US); Molly Ann Megna, Denver, CO (US); Katherine M. Puckett, Denver, CO (US); Wade Schutte, Denver, CO (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 422 days.

(21) Appl. No.: 17/392,849

(22) Filed: Aug. 3, 2021

(65) Prior Publication Data

US 2023/0040816 A1 Feb. 9, 2023

(51) Int. Cl.
*A61B 18/14* (2006.01)
*A61B 17/00* (2006.01)
(Continued)

(52) U.S. Cl.
CPC ...... *A61B 18/1487* (2013.01); *A61B 18/1482* (2013.01); *A61B 2017/00685* (2013.01);
(Continued)

(58) Field of Classification Search
CPC ............ A61B 18/1487; A61B 18/1482; A61B 2017/00685; A61B 2018/00029;
(Continued)

(56) References Cited

U.S. PATENT DOCUMENTS

| | | | | |
|---|---|---|---|---|
| 5,215,521 A | * | 6/1993 | Cochran | .......... A61B 17/00234 383/73 |
| 6,517,498 B1 | * | 2/2003 | Burbank | .......... A61B 17/32056 606/45 |

(Continued)

OTHER PUBLICATIONS

International Search Report and Written Opinion from PCT Application PCT/IB2022/057172, dated Nov. 10, 2022, 15 pgs.

(Continued)

*Primary Examiner* — Eun Hwa Kim
*Assistant Examiner* — Catherine C. Premraj
(74) *Attorney, Agent, or Firm* — Husch Blackwell LLP

(57) ABSTRACT

An electrosurgical device including an elongated body extending from a proximal portion to a distal portion and defining an internal passageway configured to convey tissue from the distal portion to the proximal portion; a coring electrode at the distal portion of the elongated body, where the coring electrode is positioned at an opening to the internal passageway, and where the coring electrode is configured to deliver electromagnetic energy to adjacent tissue to cut a volume of the tissue as the tissue is conveyed into the internal passageway; and a powered conveyance mechanism positioned within the internal passageway configured to further cut the volume of the tissue and convey the volume of the tissue proximally within the internal passageway.

20 Claims, 9 Drawing Sheets

(51) Int. Cl.
   *A61B 18/00*        (2006.01)
   *A61B 18/12*        (2006.01)
(52) U.S. Cl.
   CPC .............. *A61B 2018/00029* (2013.01); *A61B 2018/00202* (2013.01); *A61B 2018/00577* (2013.01); *A61B 2018/00601* (2013.01); *A61B 2018/0091* (2013.01); *A61B 2018/1253* (2013.01); *A61B 2018/126* (2013.01); *A61B 2218/007* (2013.01)
(58) Field of Classification Search
   CPC   A61B 2018/00202; A61B 2018/00577; A61B 2018/00601; A61B 2018/0091; A61B 2018/1253; A61B 2018/126; A61B 2218/007
   See application file for complete search history.

(56)                References Cited

U.S. PATENT DOCUMENTS

| 7,241,293 | B2 | 7/2007 | Davison |
| 8,177,783 | B2 | 5/2012 | Davison et al. |
| 9,023,040 | B2 | 5/2015 | Bloom et al. |
| 2001/0001124 | A1 | 5/2001 | Mueller |
| 2002/0143289 | A1 | 10/2002 | Ellis et al. |
| 2002/0193705 | A1 | 12/2002 | Burbank et al. |
| 2005/0165345 | A1* | 7/2005 | Laufer ........... A61B 17/320016 |
| | | | 604/26 |
| 2011/0282324 | A1* | 11/2011 | Kurokawa ....... A61B 17/12186 |
| | | | 604/514 |
| 2013/0220524 | A1* | 8/2013 | Zeroni ................... B29C 65/18 |
| | | | 156/221 |
| 2014/0277039 | A1* | 9/2014 | Liberatore ....... A61B 17/32053 |
| | | | 606/167 |
| 2016/0278844 | A1 | 9/2016 | Zamarripa et al. |
| 2017/0303995 | A1 | 10/2017 | Garrison et al. |
| 2020/0330156 | A1 | 10/2020 | Brown et al. |

OTHER PUBLICATIONS

International Search Report and Written Opinion from PCT Application PCT/IB2022/057219, dated Nov. 10, 2022, 15 pgs.
Application and file history for U.S. Appl. No. 17/392,889, filed Aug. 3, 2021, inventors Greeley et al.

\* cited by examiner

ENERGIZED CORERS WITH POWERED CONVEYING

FIELD

This invention relates generally to surgical methods and apparatuses and particularly to electrosurgical devices.

BACKGROUND

Electrosurgical devices such as plasma-mediated thermo-electric cutting devices have been developed for use in cutting soft biological tissue in surgical settings. Such devices have found use in various surgical settings and procedures including, but not limited to, spine discectomy and fusion, and other surgical specialties such as general surgery, breast, thoracic, general surgeries and the like. Typically, such electrosurgical devices are classified as being either a monopolar or bipolar electrosurgical devices. A monopolar device generally includes a single electrode at the device and configured to communicate with a reference electrode, typically in the form of a pad, attached to the exterior of a patient. Monopolar electrosurgical devices deliver highly concentrated electrical energy that enhances cutting edges to excise material and then transmits through the tissue of a patient. In contrast, a bipolar electrosurgical device includes a pair of electrodes carried by the device and positioned in close proximity to one another. Bipolar electrosurgical devices may utilize lower energy levels, compared to monopolar devices, and may be better suited for heating or coagulation. Further, bipolar electrosurgical devices may be better suited for wet field application and localized heating.

SUMMARY

The techniques of this disclosure generally relate to electrosurgical cutting devices with a coring tip that can be adapted for monopolar or bipolar functionality. The disclosed devices may also include one or more additional electrodes configured to help excise and remove material without clogging. While the devices may be used in a variety of surgical procedures, the disclosed devices may be particularly suited for discectomy procedures or those where preservation of tissue directly adjacent to the cutting site is important for success of the procedure.

In an embodiment, the disclosure describes an electrosurgical device including an elongated body extending from a proximal portion to a distal portion and defining an internal passageway configured to convey tissue from the distal portion to the proximal portion; a coring electrode carried by the distal portion of the elongated body, where the coring electrode is positioned at an opening to the internal passageway, and where the coring electrode is configured to deliver electromagnetic energy to tissue adjacent to the coring electrode to cut a volume of the tissue and convey the volume of the tissue into the internal passageway; and a powered conveyance mechanism positioned within the internal passageway configured to further cut the volume of the tissue and convey the volume of the tissue proximally within the internal passageway.

In another embodiment, the disclosure describes a method of performing electrosurgery on soft tissue that includes delivering electromagnetic energy to adjacent tissue using a coring electrode of an electrosurgical device to cut a volume of the tissue, where the electrosurgical device comprises an elongated body extending from a proximal portion to a distal portion and defining an internal passageway configured to convey tissue from the distal portion to the proximal portion, the a coring electrode carried by the distal portion of the elongated body, and a powered conveyance mechanism positioned within the internal passageway configured to further cut the volume of the tissue and convey the volume of the tissue proximally within the internal passageway. The method also includes mechanically cutting of tissue into two or more pieces using the powered conveyance mechanism.

In another embodiment, the disclosure describes an electrosurgical device including an elongated body extending from a proximal portion to a distal portion and defining an internal passageway configured to convey tissue from the distal portion to the proximal portion; a coring electrode positioned at the distal portion of the elongated body, where the coring electrode is positioned at an opening to the internal passageway, and where the coring electrode is configured to deliver electromagnetic energy to adjacent tissue to cut a volume of the tissue as the volume of the tissue is conveyed into the internal passageway; an internal electrode positioned within the internal passageway and configured to deliver electromagnetic energy to the volume of the tissue to further cut or reduce a size of the volume of the tissue; and a powered conveyance mechanism positioned within the internal passageway configured to further cut the volume of the tissue and convey the volume of the tissue proximally within the internal passageway.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The disclosure can be more completely understood in consideration of the following detailed description of various embodiments of the disclosure, in connection with the accompanying drawings, in which.

Figure 1:
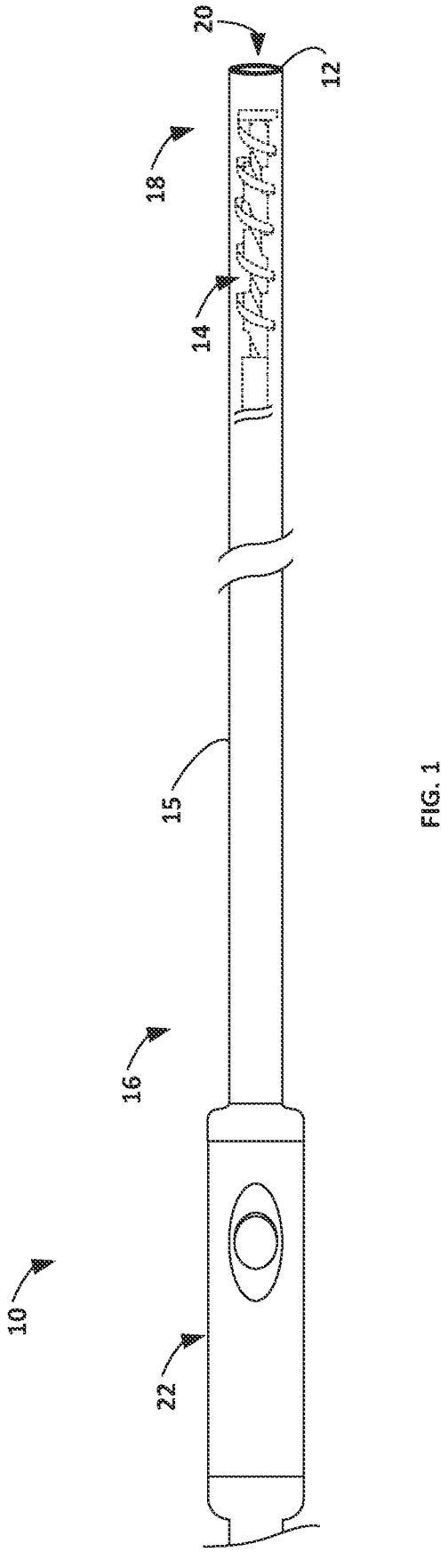
FIG. 1 is a schematic view of an example electrosurgical device that includes a coring electrode tip and powered conveyance mechanism.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

FIG. 1 is a schematic view of an example electrosurgical device 10 as described herein that includes a coring electrode 12 tip and powered conveyance mechanism 14 that may be used with electrosurgical procedures including, for example, performing a discectomy. A discectomy procedure involves the surgical removal of an intervertebral disc and fusion of adjacent vertebra. Intervertebral discs are flexible pads of fibro cartilaginous tissue tightly fixed between the vertebrae of the spine. The discs comprise a flat, circular capsule roughly 1 to 2 inches in diameter and about 0.25 to 0.5 inches thick and made of a tough, fibrous outer membrane called the annulus fibrosus, surrounding an elastic core called the nucleus pulposus. Under stress, it is possible for the annulus fibrosus to fail or the nucleus pulposus to swell and herniate, pushing through a weak spot in the annulus fibrosus membrane of the disc and into the spinal canal. Consequently, all or part of the annulus fibrosus and/or nucleus pulposus material may protrude through the weak spot, causing pressure against surrounding nerves which results in pain and immobility.

Where a damaged intervertebral disc must be removed from the patient as part of a discectomy and a subsequent fusion of vertebral bodies of the superior and inferior vertebrae, the surgeon may first retract soft tissue from the point of entry to the vertebrae to be fused. Around and attached to the vertebrae are, among other things, various muscles which act on the vertebrae to affect movement of the upper body. Once the retraction is complete, and the disc is exposed, the disc may be removed. The vertebrae may then be aligned to straighten the spinal column, and stabilized relative to one another by rods or other supports which are attached to the vertebrae by numerous fastening techniques. The surgeon may then place implants and bone grafts across the exposed surfaces of adjoining vertebrae and restore the location of the soft tissue to cover the bone graphs and vertebrae. The grafts regenerate, grow into bone and fuse the vertebrae together, with the implant and rod functioning as a temporary splint which stabilizes the spinal column while the bone fuses together over a period of months.

During the discectomy and fusion, the disclosed devices may be particularly useful to separate and remove the intervertebral disc without damage to the adjacent tissue and bone. Further, during a discectomy, blood vessels are often cut, ruptured or otherwise severed. These blood vessels bleed, and the resulting blood can flow into the tissue treatment site making visibility more difficult and prolonging the procedure. In some examples, the devices may also be used to shrink and seal blood vessels of the vertebral venous and/or arterial systems against blood loss before or after the vessels are cut, rupture or are otherwise severed.

Electrosurgical device 10 includes an elongated body 15 extending from a proximal portion 16 to a distal portion 18 that defines an internal passageway 20 configured to convey excised tissue from distal portion 18 to the proximal portion 16. Electrosurgical device 10 may be configured such that proximal portion 16 of elongated body couples with a handle assembly 22, which in turn is configured to couple to an electrosurgical power supply (not shown) that delivers the electromagnetic energy to coring electrode 12. The electrosurgical power supply may be configured to generate and provide radiofrequency (RF) monopolar energy, bipolar energy, or the option to select between either. Handle assembly 22 may also include one or more finger switches or buttons 26 for activating device 10 to deliver the desired electrosurgical energy to the adjacent tissue via one or more of the disclosed electrodes. Additionally, or alternatively, handle assembly 22 can include a stand or mount for stabilizing device 10 during an electrosurgical procedure. additional switches or buttons for actuating other features of device 10, additional connectors for coupling device 10 to other components (e.g., negative pressure pump and reservoir) for use during the procedure, and the like.

Coring electrode 12 is at distal portion 18 of elongated body 15 and configured to deliver electromagnetic energy (e.g., RF plasma, including a pulsed electron avalanche plasma, or ablation energy) to surrounding patient tissue (e.g., soft tissue or disc material) to cut a volume of the tissue as said volume is conveyed into internal passageway 20. In some examples, the opening that provides entry to internal passageway 20 may defined at least in part by the geometry of coring electrode 12. As electromagnetic energy is delivered to the surrounding soft tissue, coring electrode 12 cuts the adjacent tissue to create a volume of the tissue (e.g., excised tissue) that enters through the opening defined by coring electrode 12 and is conveyed into internal passageway 20.

Coring electrode 12, as well as the other electrodes described herein, may be composed of any suitable conductive material including, but not limited to, stainless steel, titanium, platinum, iridium, niobium or alloys thereof. Other components of device 10, including elongated body 15, can be fabricated from biologically acceptable materials suitable for medical applications, including metals, synthetic polymers, ceramics, and combinations thereof. For example, the components of elongated body 15 can be fabricated from materials such as stainless steel alloys, thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), semi-rigid and rigid materials, elastomers, rubbers, thermoplastic elastomers, thermoset elastomers, elastomeric composites, rigid polymers including polyphenylene, polyamide, polyimide, polyetherimide, polyethylene, and combinations thereof. Preferably, elongated body 15 is constructed to produce a rigid or resilient body capable of withstanding the longitudinal forces applied by the clinician during tissue removal without bending or kinking elongated body 15. Further, exposed surfaces of elongated body 15 (apart from the surfaces produced by the electrodes) should be electrically insulated from the disclosed electrode(s). In some embodiments, the efficiency of energy delivery into tissue by coring electrode 12 or other electrodes described may be further regulated by the strategic use of coating materials such as ceramic, glass, or dielectric coatings to electrically insulate portions of the described electrode(s) or portions of elongated body 15 to control the surface area or separation distances.

Depending on the configuration of electrosurgical device 10 coring electrode 12 may be configured as a monopolar electrode or bipolar electrode, or configured to operate in either configuration depending on user selection. For example, coring electrode 12 may communicate with a reference electrode (not shown) such as a back plate, or topical pad connected to electrosurgical power supply to provide a monopolar arrangement. Additionally, or alternatively, coring electrode 12 may communicate with one or more of the other electrodes along elongated body 15 that are described further below to provide an arrangement for the delivery of the electromagnetic energy in a bipolar configuration. As used herein, the term "reference electrode" is used to signify an electrode configured to communicate with one of the electrodes along elongated body 15 in a monopolar arrangement and is itself not carried by elongated body 15. Similarly, when an electrode is said to function in a monopolar arrangement, the electrode is configured to communicate with a reference electrode that is not carried by elongated body 15. The electromagnetic energy may be delivered in the form of radio frequency or pulsed radio frequency energy delivery to cut through surrounding soft tissue.

In a monopolar electrosurgical configuration, the active electrode, such as coring electrode 12, is positioned at the target surgical site. The reference electrode such as a dispersive pad, may be placed somewhere on the patient's body. Electrical current passes through the patient as it completes the electrical circuit from the active electrode to the reference electrode. The reference electrode has a much larger conductive surface area compared to the active electrode to help safely dissipate the electrical energy and prevent localized heating. In contrast, the active electrode has a much smaller surface area allowing for significant plasma or current to be produced at the treatment site to produce cutting, ablation, or coagulation affects. The electric current may be concentrated in the area of contact of the active electrode offering versatility and function with a variety of electrosurgical waveforms to produce different tissue effects. Monopolar electrosurgical configuration may be particularly useful in dry field plasma cutting and may be extended to wet field plasma cutting via waveform modification.

In a bipolar electrosurgical configuration, both the electrodes (e.g., active and return) are positioned in close proximity to one another at the target treatment site. Only the tissue spanning the distance between the two electrodes becomes included in the electrical circuit. Bipolar electrosurgery may offer advantages by permitting operation in a variety of mediums including wet field operation. In a wet field application, current may flow not only through the tissue but also through the fluid surrounding the tissue, and thus more energy will be dispersed at the site. The additional energy in wet field applications may permit coagulation or sealing in such environments. Further, the close proximity of the bipolar electrodes provides advantages in monitoring or interrogating various electrical properties of the adjacent tissue (e.g., tissue electrical resistivity and impedance) to provide more accurate an assessment of the adjacent tissue integrity, composition, or both.

During operation, coring electrode 12 defines a cutting edge. However, in contrast to the mechanical edge for a knife, the cutting edge of coring electrode 12 delivers targeted and focused RF energy to the desired surgical site. Hence the edge produced by coring electrode 12 may be tapered, rounded, flat, or sharp, but need not be of any particular dimension or sharpness. The tissue cutting may be assisted by mechanical force supplied by the clinician, the shape and configuration of coring electrode 12 providing tactile feedback to the user.

In some embodiments, particularly in use of discectomy procedures that include delicate adjacent tissue, to help decrease heat accumulation and associated collateral tissue damage, low voltage, current, power and/or low duty cycle waveforms may be used. Low power waveforms typically refer to low voltage, continuous waveforms. Low duty-cycle here typically refers to the proportion of time that the energy is actually being applied and may include cycles of less than 10% which may be, for instance, 1% or less, or 0.1% or less. A pulsed low duty-cycle signal may include a plurality of pulse bursts that are separated by more than one millisecond (e.g., has a frequency of less than 1 kHz) where each burst is shorter than one millisecond which may assist in minimizing tissue charring or burning.

The electrical signals suitable to create a plasma cutting effect are well known in the field. For instance, in the example of an applied RF (radio frequency) signal, the signal may have a frequency in the range of 100 kHz to 10 MHz applied in continuous or bursted or pulsed waveforms. Each burst typically has a duration in the range of 10 microseconds to 1 millisecond with each burst having a duty duration of about 0.1 to 10 microseconds. The pulses may be bi-phasic square waves that alternate positive and negative amplitudes. The interval between pulses should be shorter than a lifetime of the plasma vapor cavity in order to maintain the cavity and the plasma regime during each pulse burst. The time between the pulse bursts is sufficient so that the duty-cycle is relatively low. This minimizes the undesirable heating effects. Additional details regarding bipolar versus monopolar electrode selections and cutting versus coagulation operational parameters are described in U.S. Pat. No. 8,177,783 B2 entitled "Electric plasma-mediated cutting and coagulation of tissue and surgical apparatus," the entire contents of which is incorporated by reference.

Figure 2A:
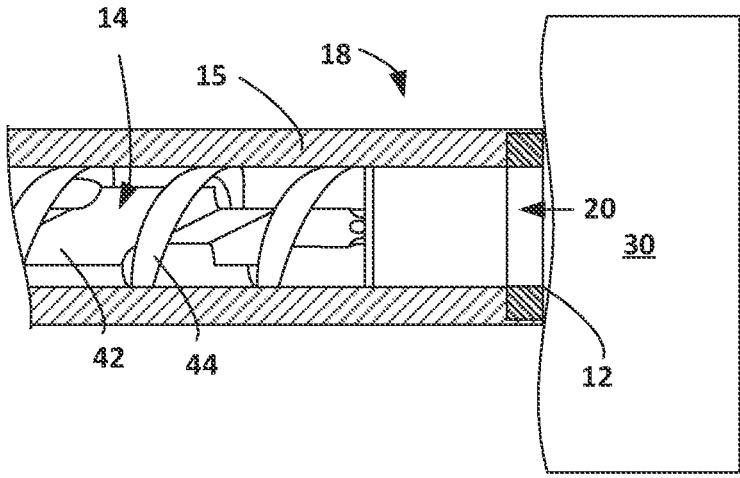
FIGS. 2A and 2B are schematic cross-sectional views of a distal portion of an elongated body illustrating cutting features of a coring electrode that may be used with the electrosurgical device of FIG. 1.
Figure 2B:
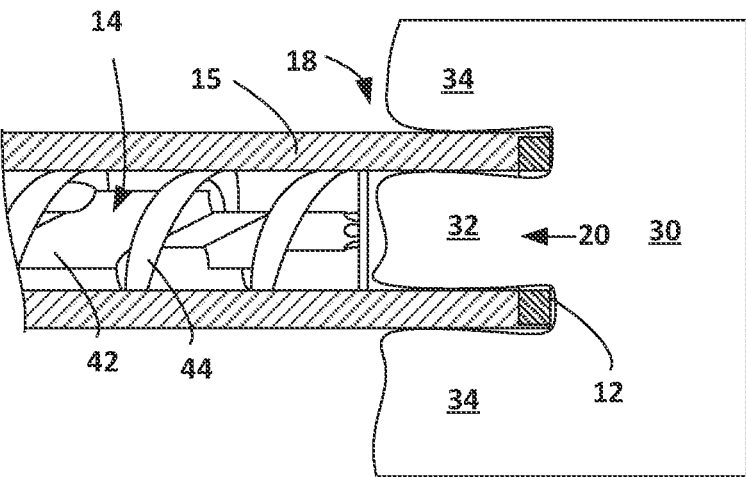

FIGS. 2A and 2B are schematic cross-sectional views of distal portion 18 illustrating cutting features of coring electrode 12 during operation. The configuration of coring electrode 12 defines an opening that provides entry into internal passageway 20. As electromagnetic energy is delivered to the surrounding soft tissue 30, coring electrode 12 cuts the adjacent tissue 30 to create a volume of the tissue (e.g., excised tissue 32) that enters through the opening defined by coring electrode 12 and is conveyed into internal passageway 20. Excised tissue 32 may be separated from tissue 30 by various means including briefly pausing forward motion and allowing the energy to cut across the inner radius of electrode 12 or slightly tilting or transversely moving electrode 12 to cut the base of 32. The adjacent tissue 34 is preserved and passes along the exterior elongated body 15.

Figure 2C:
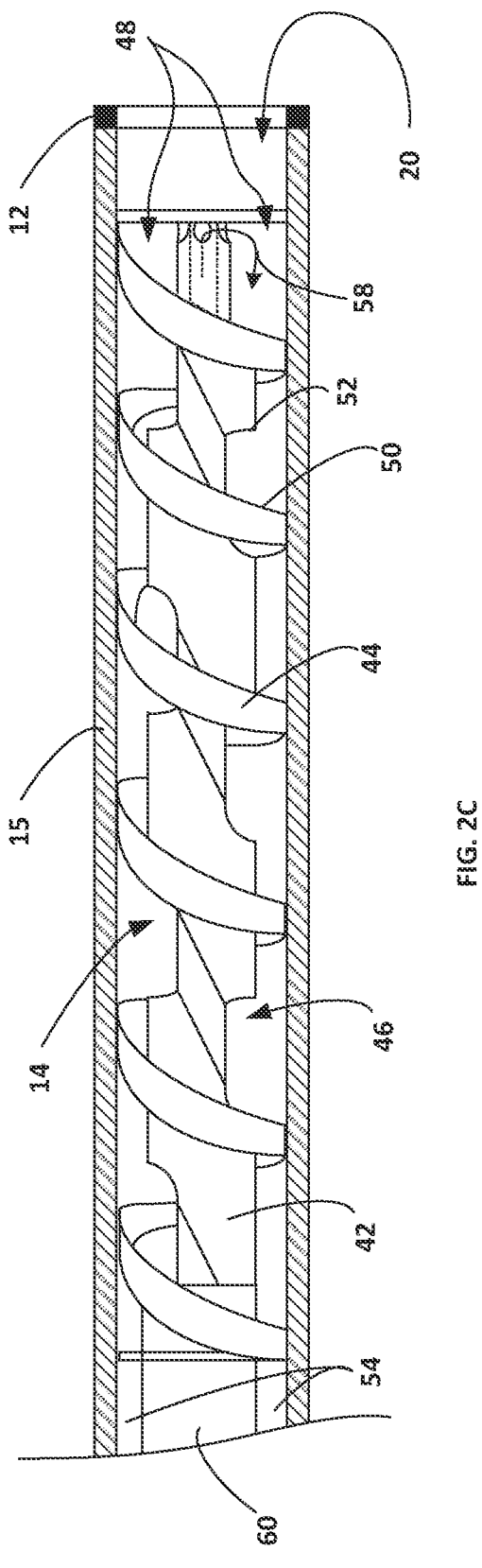
FIG. 2C is schematic view of the distal portion of the elongated body illustrating features of the powered conveyance mechanism that may be used with the electrosurgical device of FIG. 1.

To maintain continuous flow of excised material 32 or help expedite its removal through internal passageway 20, the disclosed electrosurgical devices 10 also include powered conveying mechanism 14 within internal passageway 20. Powered conveying mechanism 14 may help further cut, extrude, emulsify, or otherwise break up excised material 32 and mechanically convey the material proximally through elongated body 15. FIG. 2C is a schematic partial cross-sectional view of distal portion 18 illustrating features of powered conveying mechanism 14.

Distal portion 18 includes coring electrode 12 and powered conveying mechanism 14 disposed within internal passageway 20 of elongated body 15. Powered conveying mechanism 14 may include an auger 42 and a blade 44 aligned coaxially within internal passageway 20. Blade 44 and auger 42 may each be in the form a helix configured to rotate relative to one another about a common axis (e.g., the longitudinal axis of elongated body 15). In some examples, blade 44 may be disposed at alternate relative orientations, such as, for example, parallel, transverse or other angular orientations such as acute or obtuse, co-axial or may be offset or staggered relative to the pitch and design of auger 42.

Auger 42 may define flutes or channels 46 within the body of auger 42 due to the helical shape for receiving and conveying portions of excised material 32 proximally within elongated body 15. While the below description primarily describes auger 42 as being stationary relative to elongated body 15 and blade 44 as rotating relative to auger 42, in other examples auger 42 may rotate relative to blade 44 with blade 44 being stationary relative to elongated body 15, or both blade 44 and auger 42 may rotate relative to each other (e.g., rotate in opposing clockwise and counterclockwise directions) and relative to elongated body 15.

In some examples of operation of device 10, excised material 32 will pass through the distal opening after being cut by coring electrode 12, where the material will then pass along the external surface of auger 42 through pathways 48. In some examples, blade 44 may be configured for rotation within passageway 48 about auger 42. As blade 44 rotates about auger 42, the blade 44 will help draw excised material 32 into channels 46 of auger 42. Blade 44 will continue to rotate whereon the leading edge 50 of blade 44 will contact portions (e.g., contact edge 52) of the exterior surface of auger 42 to create a mechanical shearing force such that leading edge 50 will cut or sever the portions of received excised material 32 and separate the material from the bulk matter entering through the distal opening. The relative rotation of blade 44 about auger 42 may help to continue the conveyance of severed excised material 32 proximally through elongated body 15 where the material is eventually drawn through proximal channel 54 and collected and properly disposed. In some examples, the relative action between auger 42 and blade 44 may help scrape or cut excised tissue into smaller sizes or even create an emulsion of excised material for easy proximal transport and removal.

In some examples, auger 42 is integrally or monolithically formed with elongated body 15 such that auger 42 is permanently affixed to body 15. For example, as described further below, the distal end of auger 42 may be fixed to a supporting member (e.g., support member 102). The proximal end of blade 44 may be coupled to a rotating shaft 60 and a motor (not shown) that mechanically rotates blade 44 about auger 42. In some embodiments, shaft 60 may be removably coupled to the motor such that shaft 60 can be removed from the motor without damaging shaft 60. Device 10 may also have one or more controls configured to actuate the operation of the motor or speed of rotation of powered conveyance mechanism 14. In some examples, the actuation may be in the form of one or more hand operated switches on handle assembly 22, a foot operated pedal, combinations thereof, and the like.

Auger 42 and blade 44 may be constructed using one or more resilient materials including one or more biologically acceptable materials suitable for medical applications. Such materials may include metals, synthetic polymers, ceramics, and combinations thereof.

In some examples, to help facilitate conveyance of excised tissue 32 along internal passageway 20 and toward proximal portion 16, device 10 may be coupled (e.g., coupled at handle assembly 22) to a negative pressure source and collection chamber to provide suction and collection of the excised material. The negative pressure source (e.g., vacuum or pump) may work in conjunction with powered conveyance mechanism 14 to facilitate the proximal flow of excised material 32 contained within internal passageway 20. The negative pressure source may be in fluid communication with proximal channel 54. The force of suction or suction and fluid (if used) suction created by the negative pressure source directs the cut tissue and fluid through proximal channel 56 to a collection assembly. Additionally, or alternatively, the suction may help to draw bulk tissue 30 into the distal opening of elongated body 15 such that the tissue is drawn in to contact with coring electrode 12 and cut.

Additionally, or alternatively, removal of excised material 32 may be further enhanced by delivering a fluid such as saline within internal passageway 20, to the treatment site where the cutting occurs, or both to help encourage the passage of excised material 32 into internal passageway 20. The fluid may also help cool and lubricate powered conveyance mechanism 14 to prevent overheating or seizing between the rotating parts. In some examples, auger 42 may define an internal passageway 58 configured to permit the delivery of the fluid to one or more exits positioned along auger 42, such as near the distal end of the auger. Additionally, or alternatively, elongated body 15 may define one or more fluid channels for the delivery of such fluid. As mentioned above, the fluid may mix with excised material 32 to help draw if proximally and facilitate cutting or emulsifying the excised material.

In some embodiments, the fluid may also aid in maintaining a desired electrical resistivity and impedance between coring electrode 12 and adjacent tissue 30. For example, elongated body 15 may define one or more optional fluid delivery channels 24 configured to irrigate (indicated by the arrows in FIG. 2A) the cutting site and deliver such fluids to the site during the electrosurgical procedure or irrigate internal passageway 20. The delivery of saline to the surgical site may also help introduce a conductive medium to the tissue site for wet field electrosurgery including wet field plasma cutting. However, the introduction of a conductive fluid such a saline may introduce certain drawbacks with the procedures because the fluid can obscure the surgical field and complicate the surgical procedure. Further, if such fluid is used, the fluid must be kept replenished to prevent breakdown in the plasma regime. Also, electric current flowing through the conductive fluid away from the tissue can result in unnecessary power dissipation during cutting or an increase in collateral thermal damage to surrounding/adjacent tissue for example, the spinal cord. Tissue associated with joints and discs are typically high in dissolved salts or other ions and hence relatively electrically conductive and may not need further introduction of conductive fluids. Thus, the fluid delivery channels 24 and the delivery of fluids such as saline represent an optional feature and may be used in conjunction with any of the devices described whether or not they are expressly described with such devices or depicted in the accompanying figures.

In some embodiments, to further assist with the removal of excised material through internal passageway 20, the disclosed electrosurgical devices 10 may also include at least one internal electrode positioned within internal passageway 20. As discussed further below, the internal electrode(s) assembly may be configured to deliver electromagnetic energy to the excised volume of tissue 32 to further cut, reduce the size, or otherwise break apart the volume of excised tissue 32 initially cut by coring electrode 12, thereby aiding in the conveyance of the volume of tissue through the internal passageway 20. In some embodiments, blade 44 may be configured as the internal electrode to function in connection with coring electrode 12 or other electrodes within internal passageway (e.g., bipolar arrangement) or in connection with a reference electrode (e.g., monopolar arrangement). In some such examples, blade 44 may be electrically coupled through shaft 60 or other conductive elements contained in elongated body 15.

Figure 3A:
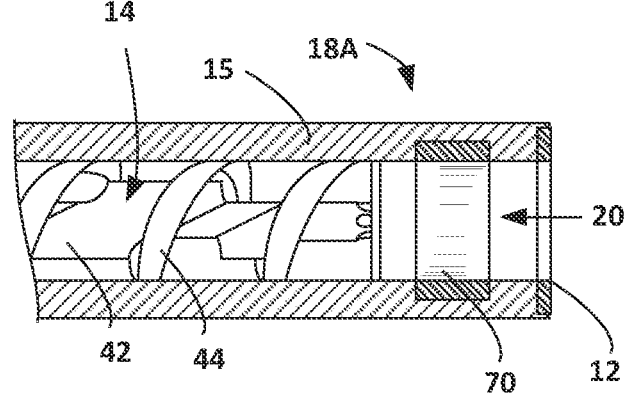
FIGS. 3A and 3B are schematic views of another distal portion of an elongated body that includes a coring electrode as well as at least one internal electrode positioned along the elongated body that may be used with the electrosurgical device of FIG. 1.
Figure 3B:
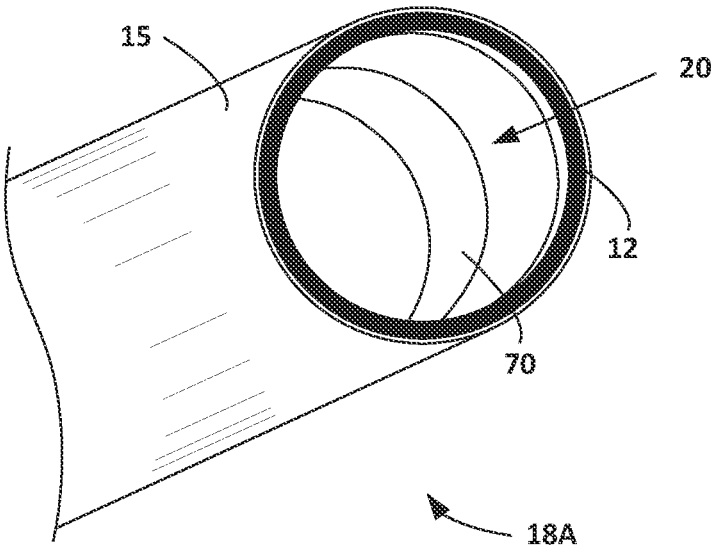

FIGS. 3A and 3B are schematic views including a cross-sectional view (FIG. 3A) and perspective view (FIG. 3B) of another distal portion 18A of an elongated body 15 that can be used with device 10. Distal portion 18A includes coring electrode 12, powered conveyance mechanism 14, as well as at least one internal electrode 70 positioned within internal passageway 20 distal relative to powered conveyance mechanism 14. Coring electrode 12 may be as described above and configured to operate in a monopolar configuration with a reference electrode or a bipolar configuration with internal electrode 70 or another electrode along elongated body 15 to cut adjacent tissue.

The bipolar arrangement has the capability of enhancing cutting safety, particularly around nerves and delicate tissue associated with a discectomy procedure, by constraining the electric current to pass between coring electrode 12 and internal electrode 70. The bipolar arrangement may also be used to help coagulate excised or adjacent tissue. Device 10 may be configured to allow the user to select between coagulation and cutting via a switch that activates a suitable electrical signal (typically of different voltage, current, power and frequency duty-cycle, etc.) for the configuration. Internal electrode 70 may also be used to coagulate, heat or char excised tissue 32 within internal passageway 20 to reduce the tissue's overall size, thereby helping to facilitate its conveyance through internal passageway 20 and allow for easy engagement with powered conveyance mechanism 14 without clogging. Coring electrode 12 and internal electrode 70, while located closely adjacent one another, are separated by insulating (dielectric) material of elongated body 15 to prevent shorting. The inclusion of internal electrode 70 may also improve the tactile feedback provided by the device 10 during an electrosurgical procedure by reducing resistance generated by excised tissue 32.

Figure 4A:
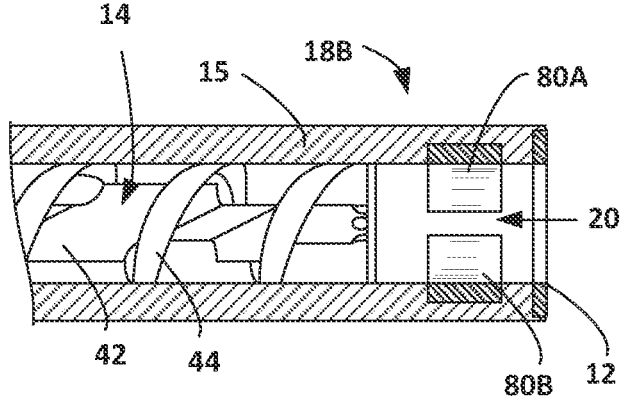
FIGS. 4A and 4B are schematic views of another distal portion of an elongated body that includes a coring electrode and a plurality of internal electrodes positioned along the elongated body that may be used with the electrosurgical device of FIG. 1.
Figure 4B:
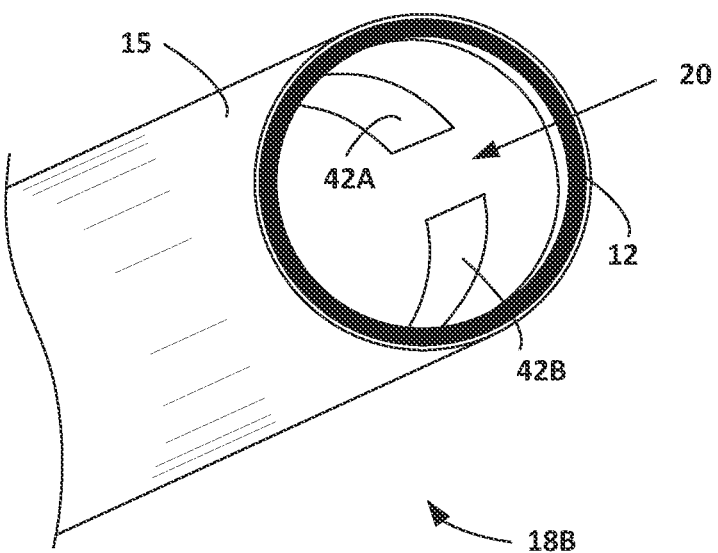

FIGS. 4A and 4B are schematic views including a cross-sectional view (FIG. 4A) and perspective view (FIG. 4B) of another arrangement of a distal portion 18B of an elongated body 15 that may be used with electrosurgical device 10. Distal portion 18B includes coring electrode 12, powered conveyance mechanism 14, and a plurality of internal electrodes 80A and 80B positioned within internal passageway 20. Coring electrode 12 and may be configured to operate in a monopolar or bipolar arrangement as described above with respect to FIGS. 3A and 3B. Additionally, or alternatively, internal electrodes 80A and 80B may be configured to operate in a bipolar configuration therebetween. For example, internal electrodes 80A and 80B may communicate with one another to deliver electromagnetic energy to excised tissue 32 to further breakdown the tissue and reduce the tissue's overall size and volume. The reduced size of excised tissue 32 may be more easily withdrawn from the cutting site and rendered by power conveyance mechanism 14 as the material proceeds proximally through internal passageway 20.

The plurality of internal electrodes 80A and 80B may be in the form of any suitable shape including, but not limited to a partial ring (e.g., partial circular or rectangular ring), curvilinear object, or bar. Further, because the internal electrodes 80A and 80B are positioned within internal passageway 20 and do not directly contact preserved tissue 34, the size and surface area of electrodes 80A and 80B may larger than that of coring electrode 12. Internal electrodes 80A and 80B may be positioned along the inner sidewall of internal passageway 20 so that the electrodes do not impinge on the passageway. Additionally, electrodes 80A and 80B may likewise be positioned distal within elongated body 15 relative to powered conveyance mechanism 14.

Figure 5A:
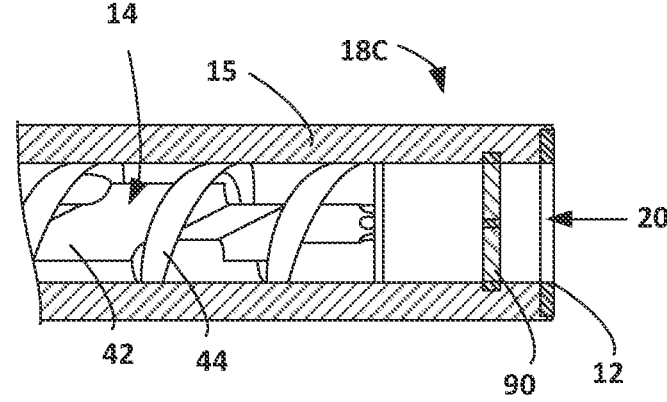
FIGS. 5A and 5B are schematic views of another distal portion of an elongated body that includes a coring electrode and at least one internal cutting electrode configured to further cut excised tissue that may be used with the electrosurgical device of FIG. 1.
Figure 5B:
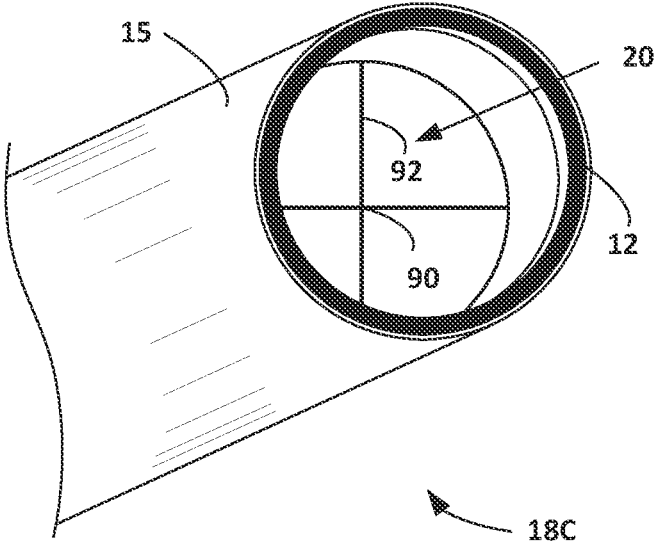
Figure 6A:
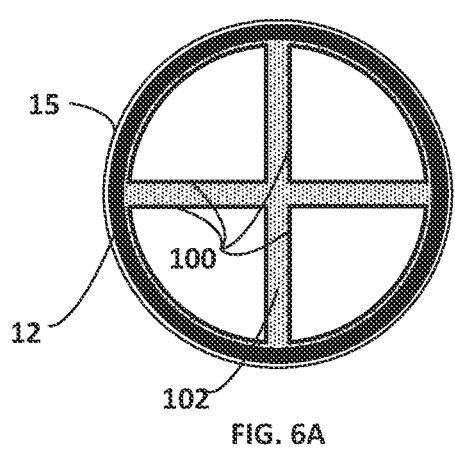
FIGS. 6A to 6C are schematic views of another distal portion of an elongated body that includes a coring electrode and a plurality of internal cutting electrodes configured to further cut excised tissue that may be used with the electrosurgical device of FIG. 1.
Figure 6B:
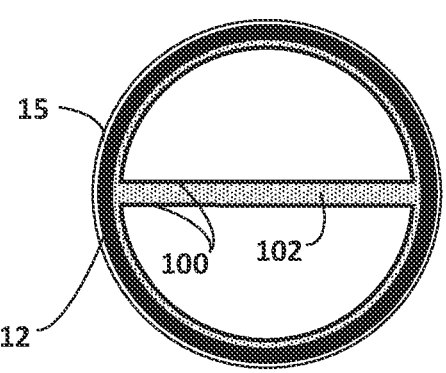
Figure 6C:
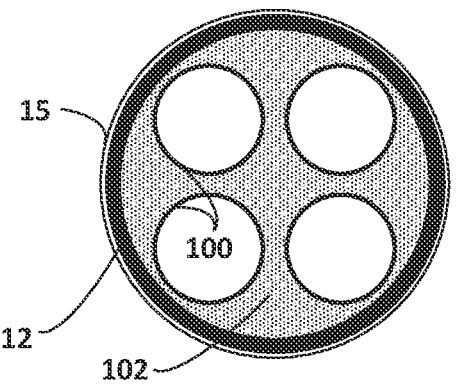

In some examples, electrosurgical device 10 may include one or more internal electrodes configured to further cut excised tissue 32 (e.g., cut the tissue beyond the cuts produced by coring electrode 12) to help separate excised tissue 32 from tissue 30 by slightly rotating the device 10 along its long axis, break apart the tissue and facilitate its passage through powered conveyance mechanism 14. FIGS. 5A and 5B are schematic views including a cross-sectional view (FIG. 5A) and perspective view (FIG. 5B) of another arrangement of a distal portion 18C of an elongated body 15 that may be used with electrosurgical device 10. Distal portion 18C includes coring electrode 12, powered conveyance mechanism 14, and internal cutting electrode 90 positioned within internal passageway 20. Coring electrode 12 may be configured to operate in a monopolar arrangement or in a bipolar arrangement cutting electrode 90, or other electrodes carried by elongated body 15, in a similar manner to that described above with respect to FIGS. 3A and 3B.

Internal cutting electrode 90 includes at least one cross member 92 that at least partially dissects the cross-section of internal passageway 20. In the illustration shown in FIG. 5B, internal cutting electrode 90 includes at least one cross member 92 that at least partially dissects internal passageway 20. As excised tissue 32 is brought into contact with cross member 92, the member delivers electromagnetic energy to the excised tissue 32 to further cut the tissue longitudinally into multiple pieces. The clinician may then partially rotate device 10 providing a lateral cut (if needed) to separate the excised tissue 32 from bulk tissue 30 allowing for the delivery of the cut tissue to powered conveyance mechanism 14.

Internal cutting electrode 90 may be configured to function as a monopolar or bipolar electrode. For example, internal electrode 90 may communicate with coring electrode 12 to deliver electromagnetic energy to excised tissue 32 to further breakdown the tissue and reduce the tissue's overall size and volume. The reduced size of excised tissue 32 may be more easily withdrawn and rendered by powered conveyance mechanism 14 as the tissue traverses proximally through internal passageway 20. Cutting electrode 90 may be composed of a wire or rigid structure the impedes on the internal passageway 20 to further dissect excised tissue 32. Cutting electrode 90 may likewise be positioned distal to powered conveyance mechanism 14.

In some examples, internal cutting electrode 90 may be composed of a plurality of electrodes. For example, FIGS.

6A-6C are schematic views of alternative configurations that each include a plurality of internal cutting electrodes 100 of various shapes and sizes. Similar to cutting electrode 90, each internal cutting electrode 100 at least partially dissects the cross-section of internal passageway 20. Electrodes 100 may also define a reduced opening compared to coring electrode 12 such that excised tissue 32 passing by the respective electrode 100 is further cut into pieces, thereby reducing the overall size of the excised tissue and making it easier to be conveyed through internal passageway 20.

The electrode designs may further include one or more rigid support members 102 of dielectric material that both support the portions of cutting electrodes 100 as well as provide electrical insulation between adjacent electrodes 100 such that the electromagnetic energy transmitted by cutting electrodes 100 must travel through excised tissue 32. In some examples, the plurality of internal cutting electrodes 100 and internal support members 102 may be constructed as an insert that is embedded in elongated body 15 such that the insert defines part of the internal passageway 20.

Due to the plurality of internal cutting electrodes 100 being present, the electrodes 100 may be easily configured in a bipolar arrangement relative to one another and/or coring electrode 12 to conveniently cut excised tissue 32. Simple rotation of internal cutting electrodes 100 during the electrosurgical procedure will disconnect excised tissue 32 from bulk tissue 30 as needed.

The configuration of rigid support member 102 and cutting electrodes 100 may also provide a coinvent means for cutting and processing with powered conveyance mechanism 14. For example, the distal end of auger 42 may be connected with rigid support member 102. Blade 44 may have a distal end with a cutting edge that rotates relative to rigid support member 102. The cutting edge of blade 44 will traverse the openings created by cutting electrodes 100 creating a shearing effect. As tissue is initially longitudinally cut by electrodes 100 and passes through the openings defined by the electrodes, the rotating distal edge of blade 44 will contact and shear the tissue by forcing the tissue against the perimeter edge of rigid support member 102 where the edge of blade 44 will apply a shearing force. The sheared tissue can then be further rendered by powered conveyance mechanism 14.

Figure 7A:
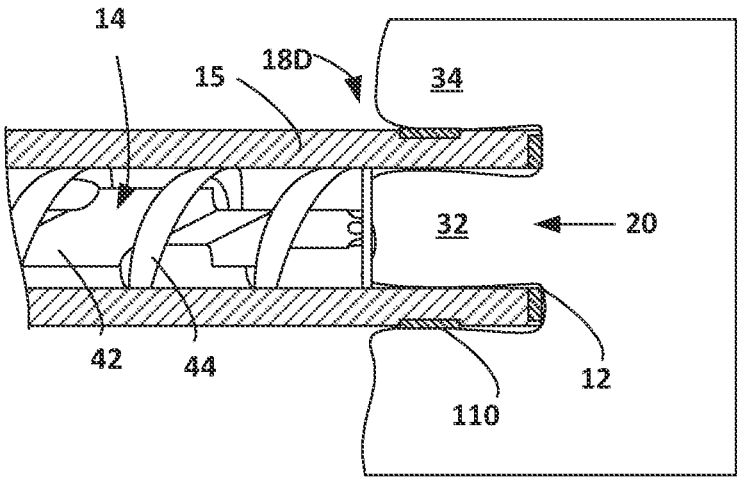
FIGS. 7A and 7B are schematic views of another distal portion of an elongated body that includes a coring electrode and at least one external electrode positioned along the elongated body that may be used with the electrosurgical device of FIG. 1.
Figure 7B:
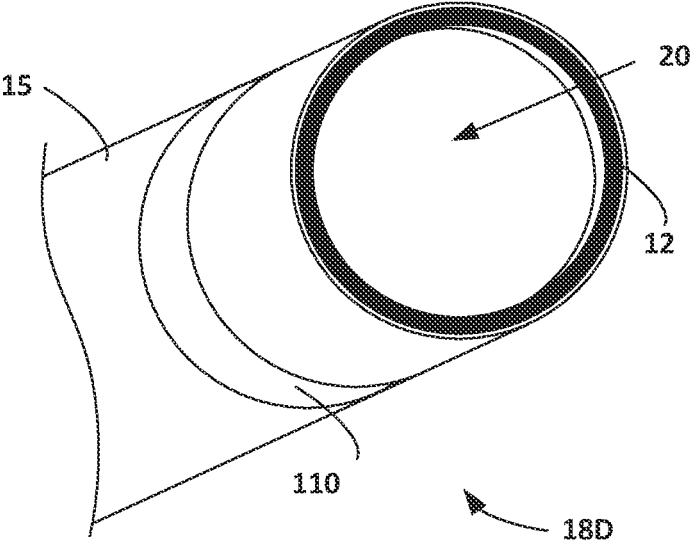

FIGS. 7A and 7B are schematic cross-sectional and perspective views respectively of another arrangement of a distal portion 18D of an elongated body 15 that may be used with electrosurgical device 10. Distal portion 18D includes one or more external electrodes 110 positioned on the exterior surface of and carried by elongated body 15. External electrode 110 may be configured to interact with adjacent tissue (e.g., preserved tissue 34) in a variety of configurations to serve one or more uses. For example, external electrode 110 may be configured to operate in a bipolar configuration with one or more of coring electrode 12 or the internal electrodes (if present) to provide field coagulation of the adjacent tissue 34. Additionally, or alternatively, external electrode 110 may be used in a sensing capacity to measure or interrogate one or more properties of adjacent tissue 34 to, for example, enhance the safety capacity of device 10 by providing more accurate feedback of the adjacent tissue such as its electrical resistivity and impedance, composition, or the like.

In some examples, it may be preferable to radially offset coring electrode 12 from the outer diameter defined by elongated body 15 such that as coring electrode 12 traverses through soft tissue 30, it does not contact adjacent tissue 34 that is intended to be preserved throughout the electrosurgical procedure. As such the largest diameter defined by the surface of electrode 12 is less than the outer diameter of distal portion 18 of elongated body 15. In some examples, the radial offset may measure about 0.2 mm to about 4.0 mm, or from about 1.0 mm to about 3.0 mm as measured in a direction perpendicular to the longitudinal axis of elongated body 15 relative to the widest part of distal portion 18.

Figure 8A:
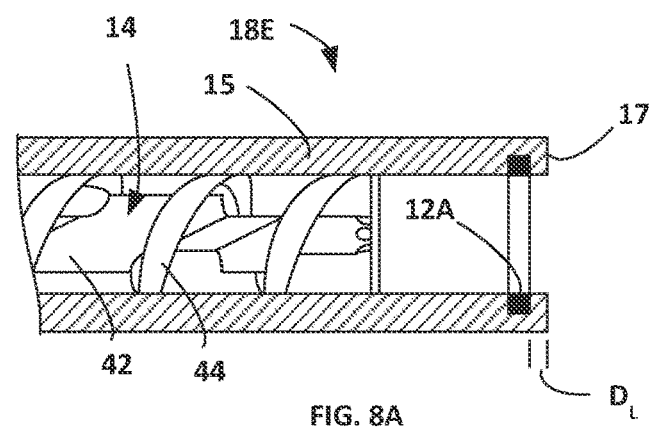
FIGS. 8A-8C are schematic cross-sectional views of another arrangement of a distal portion of an elongated body that may be used with electrosurgical device of FIG. 1 that illustrate a possible offset arrangement for the coring electrode.
Figure 8B:
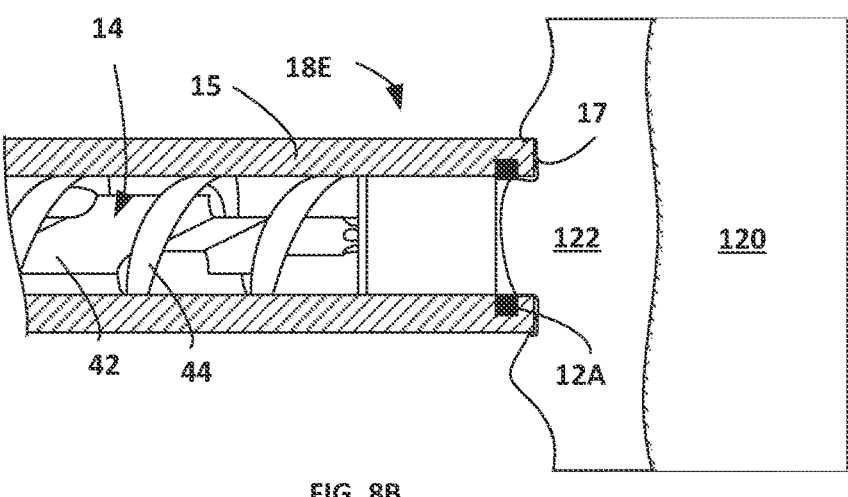
Figure 8C:
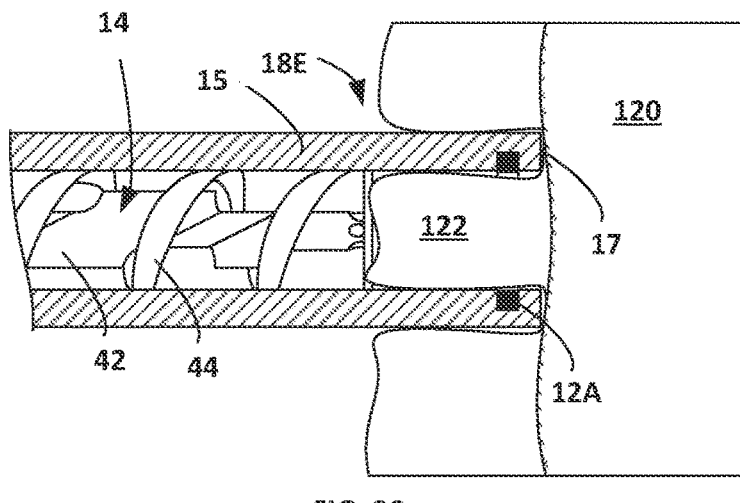

Alternatively, coring electrode 12 may be longitudinally offset so that the electrode does not form part of the distal end (e.g., distal most portion) of elongated body 15. For example, FIGS. 8A-8C are schematic cross-sectional views of another arrangement of a distal portion 18E of an elongated body 15 that may be used with electrosurgical device 10 that illustrate a possible offset arrangement for coring electrode 12A. As shown in FIGS. 8A-8C, coring electrode 12A may be longitudinally offset ($D_L$) from the distal most end 17 of elongated body 15 such that when distal most end 17 is brought into contact with a rigid surface 120, such as bone tissue (e.g., FIG. 8C), the longitudinal offset prevents coring electrode 12A from contacting rigid surface 120, even when forward force is exerted by the user.

In contrast, when contacting soft tissue 122 (e.g., FIG. 8B) intended to be excised, the soft tissue 122 may be deformed and conveyed into opening 20 where the soft tissue contacts coring electrode 12A, thereby allowing soft tissue 122 to be cut and excised in the manner described above. In some examples, the longitudinal offset may measure about 0.1 mm to about 4.0 mm, or from about 1.0 mm to about 3.0 mm as measured in a direction parallel to the longitudinal axis of elongated body 15 relative to distal end 17.

The radial or longitudinal offset design of coring electrode 12 or 12A may increase the cutting safety of electrosurgical device 10 by increasing tactile feedback and preventing damage to adjacent tissue. Such features may be particularly useful in procedures such as a discectomy where preservation of bone tissue and surrounding blood vessel or nerve clusters is desired.

The distal end 17 cross-section of elongated body 15 may take on any suitable shape and size as desired for particular applications. For example, distal end 17 may possess a circular, semi-circular, oval, curvilinear, rectangular, trapezoidal, triangular, or some other multi-faceted cross-sectional shape. The cross-section of distal end 17 may then transition to a generally round (e.g., circular) cross-section to facilitate the inclusion and operation of powered conveyance mechanism 14. In some examples, it may be useful have a combination of curved and straight sides to provide the clinician with multiple edging options for excising tissue. Further the intersections between adjacent sides may themselves be curvilinear (e.g., rounded), abrupt resulting in distinct edge transitions (e.g., the right-angle transition), or a combination of curvilinear and abrupt transitions. The selection of cross-sectional shape of distal end 17 of elongated body 15, and by association coring electrode 12, may help simultaneously improve tissue removal and tissue preservation in treatment areas having particular size or shape constraints or delicate adjacent tissue that can be easily damaged. Additionally, or alternatively, the distal opening established by coring electrode 12 may be angled relative to the longitudinal access defined by elongated body 15 such that the distal opening does not sit perpendicular to the longitudinal access of elongated body 15. Such non-perpendicular alignment of the distal opening may improve lateral movement of the distal end during tissue removal.

Various embodiments of systems, devices, and methods have been described herein. These embodiments are given only by way of example and are not intended to limit the scope of the claimed inventions. It should be appreciated, moreover, that the various features of the embodiments that have been described with respect to the different figures may be combined in various ways to produce numerous additional embodiments. For example, variations of the different electrodes may be combined with other internal electrodes, coring electrodes, external electrodes, and combinations thereof to produce an electrosurgical device tailored for a particular application or procedure. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An electrosurgical device comprising:
an elongated body extending from a proximal portion to a distal portion and defining an internal passageway configured to convey tissue from the distal portion to the proximal portion;
a coring electrode at the distal portion of the elongated body, wherein the coring electrode is positioned at an opening to the internal passageway at the distal end of the elongated body, the opening having a diameter generally equivalent to a diameter of the internal passageway, and wherein the coring electrode is configured to deliver electromagnetic energy to adjacent tissue to cut a volume of the tissue as the tissue is conveyed into the internal passageway;
a powered conveyance mechanism including an auger and a helical blade configured to rotate relative to each other in opposing directions within the internal passageway to create a shearing force so as to further cut the volume of the tissue and convey the volume of the tissue proximally within the internal passageway; and
an internal electrode positioned within the internal passageway and distal to the powered conveyance mechanism, the internal electrode coupled to at least two points of the internal passageway so as to extend across the internal passageway transverse to a longitudinal axis of the elongated body, the internal electrode configured to deliver electromagnetic energy to the volume of the tissue to further cut the volume of the tissue.

2. The electrosurgical device of claim 1, wherein the helical blade is positioned over and coaxially aligned with the auger.

3. The electrosurgical device of claim 2, wherein the auger comprises a helical shape that defines one or more flutes or channels for conveying the volume of the tissue proximally along the internal passageway.

4. The electrosurgical device of claim 2, wherein the auger defines a fluid passageway configured to deliver a fluid to one or more points along the auger to help lubricate or cool the cutting operation between the auger and the helical blade.

5. The electrosurgical device of claim 1, wherein the coring electrode is configured to operate in a monopolar configuration to cut the volume of the tissue as the tissue is conveyed into the internal passageway.

6. The electrosurgical device of claim 1, further comprising an external or second internal electrode, wherein the coring electrode is configured to operate in a monopolar configuration, or operate in a bipolar configuration with the external or second internal electrode, to cut or ablate soft tissue.

7. The electrosurgical device of claim 6, wherein the second internal electrode comprises the helical blade.

8. The electrosurgical device of claim 1, wherein the coring electrode is longitudinally offset from a distal end of the elongated body so that a distal most surface of the electrosurgical device is not defined by the coring electrode.

9. The electrosurgical device of claim 1, wherein the internal electrode comprises a plurality of internal electrodes configured to operate in a bipolar configuration relative to each other to deliver electromagnetic energy to reduce the size of the volume of the tissue conveyed into the internal passageway.

10. The electrosurgical device of claim 1, wherein the internal electrode comprises a plurality of intersecting cross members.

11. The electrosurgical device of claim 1, wherein the internal electrode comprises a plurality of internal electrodes, wherein each of the plurality of internal electrodes at least partially dissects the internal passageway, wherein the plurality of internal electrodes each define a smaller opening compared to the coring electrode, and wherein the plurality of internal electrodes are configured to operate in a bipolar configuration relative to each other to deliver electromagnetic energy to further cut the volume of the tissue conveyed into the internal passageway.

12. The electrosurgical device of claim 11, wherein the plurality of internal electrodes are supported by a dielectric support member that spans at least a portion of the internal passageway.

13. The electrosurgical device of claim 12, wherein the helical blade is configured to rotate relative to the dielectric support member to create a shearing force against the dielectric support member that further cuts the volume of the tissue.

14. The electrosurgical device of claim 1, further comprising an external electrode at the distal portion of the elongated body and defining an outer surface of the electrosurgical device, wherein the external electrode is configured to function in a bipolar configuration relative to the coring electrode or the internal electrode.

15. The electrosurgical device of claim 1, further comprising a handle assembly coupled to the proximal portion of the elongated body and configured to couple to an electrosurgical power supply that delivers the electromagnetic energy to the coring electrode and the internal electrode.

16. The electrosurgical device of claim 15, wherein the electrosurgical device is configured to be coupled to a negative pressure source to provide suction of the volume of the tissue through the internal passageway and the powered conveyance mechanism.

17. A method of performing electrosurgery on soft tissue comprising, delivering electromagnetic energy to adjacent tissue using a coring electrode and an internal electrode of an electrosurgical device to cut a volume of the tissue, wherein the electrosurgical device comprises an elongated body extending from a proximal portion to a distal portion and defining an internal passageway configured to convey tissue from the distal portion to the proximal portion, the coring electrode at the distal portion of the elongated body, wherein the coring electrode is positioned at an opening to the internal passageway, the opening having a diameter generally equivalent to a diameter of the internal passageway, and a powered conveyance mechanism including an auger and a helical blade positioned within the internal passageway configured to further cut the volume of the tissue and convey the volume of the tissue proximally within the internal passageway, the internal electrode positioned within the internal passageway and distal to the powered conveyance mechanism, the internal electrode coupled to at least two points of the internal passageway so as to extend across the internal passageway transverse to a longitudinal axis of the elongated body; and mechanically cutting tissue using the powered conveyance mechanism such that the auger and helical blade rotate relative to each other in opposing directions to create a shearing force that further cuts the volume of the tissue into two or more pieces.

18. The method of claim 17, wherein the helical blade is positioned over and coaxially aligned with the auger.

19. The method of claim 18, further comprising, delivering a fluid to one or more points along the auger to help lubricate or cool the cutting operation between the auger and the helical blade.

20. An electrosurgical device comprising:

an elongated body extending from a proximal portion to a distal portion and defining an internal passageway configured to convey tissue from the distal portion to the proximal portion;

a coring electrode at the distal portion of the elongated body, wherein the coring electrode is positioned at an opening to the internal passageway, the opening having a diameter generally equivalent to a diameter of the internal passageway, and wherein the coring electrode is configured to deliver electromagnetic energy to adjacent tissue to cut a volume of the tissue as the tissue is conveyed into the internal passageway;

an internal electrode positioned within the internal passageway and configured to deliver electromagnetic energy to the volume of the tissue to further cut or reduce a size of the volume of the tissue; and a powered conveyance mechanism including an auger and a helical blade configured to rotate relative to each other in opposing directions within the internal passageway to create a shearing force so as to further cut the volume of the tissue and convey the volume of the tissue proximally within the internal passageway, wherein the internal electrode is distal to the powered conveyance mechanism, and coupled to at least two points of the internal passageway so as to extend across the internal passageway transverse to a longitudinal axis of the elongated body.

* * * * *